US012630514B2

(12) United States Patent
Barda et al.

(10) Patent No.: US 12,630,514 B2
(45) Date of Patent: May 19, 2026

(54) PROCESS AND INTERMEDIATES FOR THE PREPARATION OF PYROXASULFONE

(71) Applicant: ADAMA AGAN LTD., Ashdod (IL)

(72) Inventors: Yaniv Barda, Rehovot (IL); Aviad Mandabi, Beer-Yaakov (IL); Carl Recsei, Tel Aviv-Jaffa (IL)

(73) Assignee: ADAMA AGAN LTD., Ashdod (IL)

( * ) Notice: Subject to any disclaimer, the term of this patent is extended or adjusted under 35 U.S.C. 154(b) by 958 days.

(21) Appl. No.: 17/630,714

(22) PCT Filed: Jul. 29, 2020

(86) PCT No.: PCT/IL2020/050836

§ 371 (c)(1),
(2) Date: Jan. 27, 2022

(87) PCT Pub. No.: WO2021/019537

PCT Pub. Date: Feb. 4, 2021

(65) Prior Publication Data

US 2022/0267279 A1 Aug. 25, 2022

Related U.S. Application Data

(60) Provisional application No. 62/880,127, filed on Jul. 30, 2019.

(51) Int. Cl.
*C07D 231/20* (2006.01)
*C07D 413/12* (2006.01)

(52) U.S. Cl.
CPC ......... *C07D 231/20* (2013.01); *C07D 413/12* (2013.01)

(58) Field of Classification Search
CPC .................................................... C07D 231/20
See application file for complete search history.

(56) References Cited

U.S. PATENT DOCUMENTS 7,488,831 B2 2/2009 Uchida
2005/0215797 A1* 9/2005 Nakatani .............. C07D 231/20 548/366.1
2012/0264947 A1 10/2012 Frasetto
2013/0015804 A1 1/2013 Kim et al.

FOREIGN PATENT DOCUMENTS

EP 1367946 A1 11/2003
EP 1541561 A1 6/2005
WO 02062770 A1 8/2002
WO 2004013106 A1 2/2004
WO 2005105755 A1 11/2005
WO 2008100426 A2 8/2008

OTHER PUBLICATIONS

Sofer, Zdenêk, et al. "The covalent functionalization of layered black phosphorus by nucleophilic reagents." Angewandte Chemie International Edition 56.33 (2017): pp. 9891-9896.
Smissman, Edward E., and John RJ Sorenson. "The Rearrangement of 1-Piperidinemethanethiol Esters," The Journal of Organic Chemistry 30.1 (1965): 300-301.
Hu, Jinbo, Wei Zhang, and Fei Wang. "Selective difluoromethylation and monofluoromethylation reactions," Chemical communications 48 (2009): pp. 7465-7478.

* cited by examiner

*Primary Examiner* — David K O'Dell
(74) *Attorney, Agent, or Firm* — FISHERBROYLES, LLP; Roger L. Browdy

(57) ABSTRACT

The invention provides a process which comprises the step of thiomethylating a pyrazole to create $R_2$—C(O)—S—$CH_2$-functionality at position 4 of the pyrazole ring. The process is useful in preparing pyroxasulfone. The invention also provides intermediates.

(III)

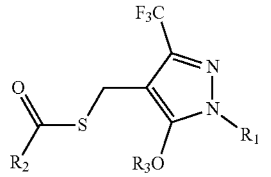

26 Claims, No Drawings

PROCESS AND INTERMEDIATES FOR THE PREPARATION OF PYROXASULFONE

Pyroxasulfone is a potent preemergent herbicide which belongs to the class of 3-([(hetero)aryl]methanesulfonyl)-4,5-dihydro-1,2-oxazole. It has the following chemical structure:

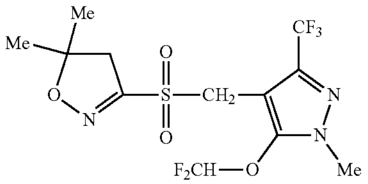

Pyroxasulfone [chemical name: 3-([5-(difluoromethoxy)-1-methyl-3-(trifluoromethyl)-1H-pyrazol-4-yl]nmethane-sulfonyl)-5,5-dimethyl-4,5-dihydro-1,2-oxazole,] was first described in WO 2002/062770 (≡EP 1364946). It is available on the marketplace as water dispersible granule and suspension concentrate.

A useful precursor of Pyroxasulfone is the corresponding sulfide of Formula 1:

1

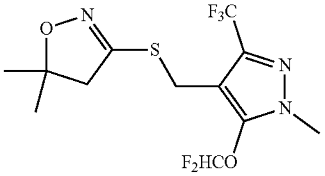

On oxidation, the sulfide of Formula 1 transforms to Pyroxasulfone, either directly or via the corresponding sulfoxide. A synthesis of the sulfide of Formula 1 was reported in WO 2004/013106 (≡EP 1541561), where thiourea was used to incorporate a sulfide functionality into the molecule. Reaction of thiourea with 4-bromomethyl-5-difluoromethoxy-1-methyl-3-trifluoromethyl-1H-pyrazole led to the displacement of the bromine and formation of 2-(5-difluoromethoxy-1-methyl-3-trifluoromethyl-1H-pyrazole-4-ylmethyl)-isothiourea, in the form of its hydrobromide salt (Example 10 of EP 1541561). In turn, this salt was combined with 3-chloro-5,5-dimethyl-2-isoxazoline in the presence of a base, to afford the sulfide of Formula 1 (Reference Example 1 of EP 1541561).

As can be seen from the chemical structure depicted above, the sulfide of Formula 1 consists of two key fragments, the isooxazole and pyrazole rings, linked together by —S—$CH_2$— bridge. We have now found a short and elegant synthetic pathway to prepare the sulfide of Formula 1; the novel synthetic pathway is applicable in fact to a broader class of sulfides of Formula I:

I

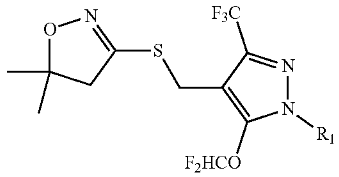

wherein $R_1$ is $C_1$-$C_3$ alkyl. As pointed out above, $R_1$ is preferably methyl. The sulfide of Formula 1 ($R_1$ is methyl) is chemically named 3-[[[5-(difluoromethoxy)-1-methyl-3-(trifluoromethyl)-1H-pyrazol-4-yl]methyl]thio]-4,5-dihydro-5,5-dimethylisoxazole}.

The sulfides of Formula I are synthetically accessible through a class of thioester intermediates of the Formula III:

III

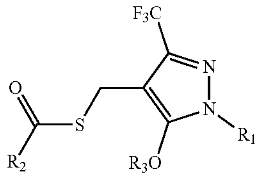

where $R_1$ is $C_1$-$C_3$ alkyl, $R_2$ is α hydrogen-bearing group (e.g., $Y_2Y_1H^*C^*$—, where the α carbon and α hydrogen are denoted by asterisks, for example, $R_2$ is —$CH_3$ or —$CH_2C_6H_5$), and $R_3$ is selected from hydrogen and $C_1$ group that is directly transformable into —$CHF_2$, as set out in more detail below.

Especially preferred are the thioesters of Formula III where $R_2$ is methyl and $R_3$ is hydrogen, i.e., the thioacetate of Formula 3 where $R_1$ is also methyl:

3

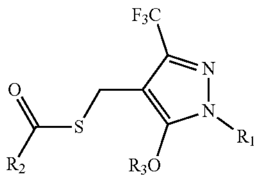

The synthetic pathway leading to the sulfide of Formula I is depicted below:

Scheme A

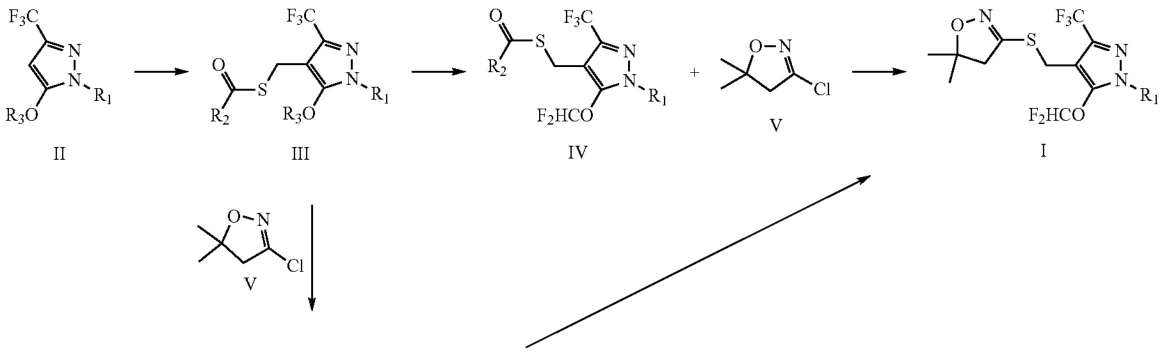

II III IV V I V

-continued

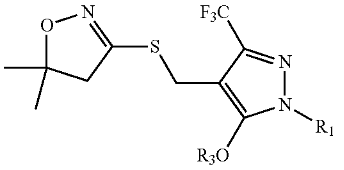

VI

The general synthetic pathway reduces to the following preferred scheme (i.e., $R_1$=$R_2$=methyl; $R_3$=H):

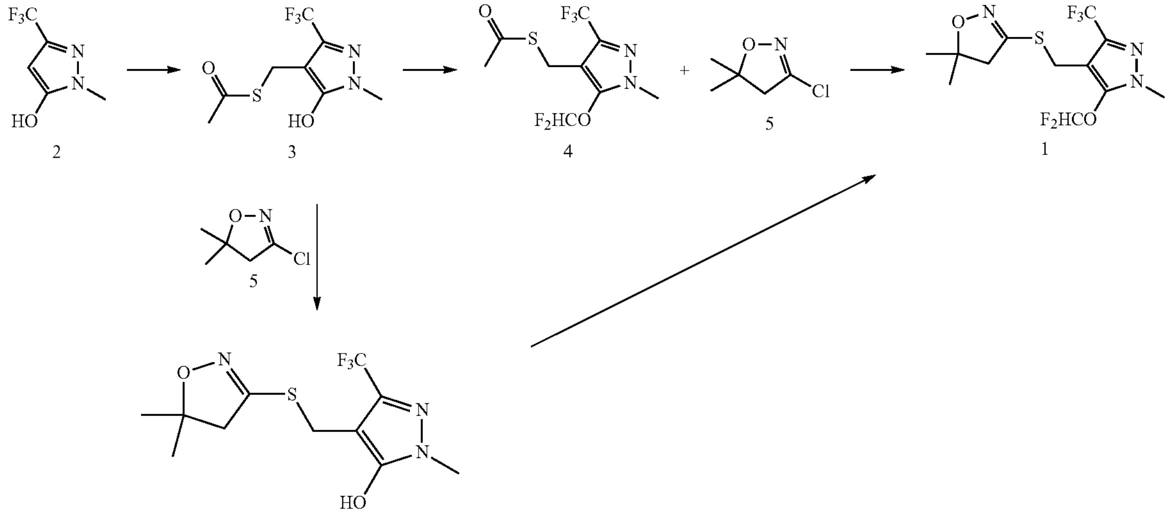

2 3 4 5 1 5 6

It is seen that the synthetic pathway encompasses two alternative routes:

II→III→IV→I (e.g., 2→3→4→1); or

II→III→VI→I (e.g., 2→3→6→1)

Each of the individual steps in the sequential reactions illustrated in Scheme A is discussed in detail below. It should be noted that the above-depicted structures are meant to include keto-enol tautomerism, where applicable.

II→III→IV→I (e.g., 2→3→4→1)

II→III (e.g., 2→3)

A primary aspect of the invention is a process comprising the step of thiomethylating a pyrazole of Formula II:

II

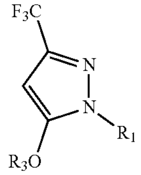

to create $R_2$—C(O)—S—$CH_2$— functionality at position 4 of the pyrazole ring, thereby obtaining, and preferably isolating, a thioester of Formula III:

III

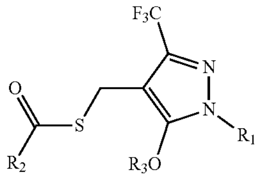

where $R_1$ is $C_1$-$C_3$ alkyl;

$R_2$ is α hydrogen-bearing group [e.g., $Y_2Y_1H^*C^*$—, such that $R_2$ is preferably $C_1$-$C_3$ alkyl ($Y_1$ and $Y_2$ are independently selected from hydrogen and $C_1$-$C_2$ alkyl) or $R_2$ is benzyl (i.e., $Y_1$ is hydrogen and $Y_2$ is —$C_6H_5$); and $R_3$ is hydrogen or $C_1$ group transformable into $F_2HC$—, said $C_1$ group being $Y_3Y_4HC$— where $Y_3$ and $Y_4$ are selected from halogen (with the exception of course of $Y_3$=$Y_4$=F), alkoxy, or said $Y_3$ and $Y_4$ are taken together to be =O (such that said $C_1$ group is a formyl group).

Hence, in its most general form, the thioester of Formula III is thioacetate ($Y_1$ and $Y_2$ are both hydrogen, such that $R_2$ is methyl) or α-substituted thioacetate (at least one of $Y_1$ and $Y_2$ is other than hydrogen).

One approach towards thiomethylation of pyrazole of Formula II involves a reaction with a compound of the formula M-S—C(O)—$R_2$, wherein M is hydrogen or a metal cation, e.g., alkali metal cation, and $R_2$ is as defined above, in the presence of formaldehyde source, preferably in an alkaline environment.

Regarding the pyrazole of Formula II starting material, it is commercially available, or can be prepared by methods known in the art, e.g., as described in WO 2004/013106 (≡EP 1541561), by the ring closure reaction of methyl hydrazine and 4,4,4-trifluoro-3-oxo-butyric acid ethyl ester. An illustrative procedure can be found in US 2013/015804 and U.S. Pat. No. 7,488,831.

Regarding the compound M-S—C(O)—$R_2$, thioacetic and α-substituted thioacetic acids (e.g., $R_2$ is —$CH_3$ or —$CH_2C_6H_5$, respectively) can be utilized in the reaction, most conveniently in their salt form (e.g., potassium thioacetate). Salts of thioacetic and α-substituted thioacetic acids are available in the marketplace and their preparation is well known [for example, Org. Synth 32, 101 (1952)]. Generally, the molar ratio between the compound M-S—C(O)—$R_2$ and pyrazole of Formula II is approximately stoichiometric. A slight excess of M-S—C(O)—$R_2$ may be employed, for example up to about 1.5:1, e.g., from 1.1:1 to 1.3:1, with ~1.2:1 ratio being most preferred.

Sources of formaldehyde include aqueous formaldehyde and paraformaldehyde. Paraformaldehyde (a polymer of the formula $HOCH_2(OCH_2)_{n-2}OCH_2OH$) gradually dissolves in an alkaline environment, undergoing de-polymerization to give formaldehyde which participates in the reaction. For example, paraformaldehyde in a powder/flaky/pelleted form with a degree of polymerization (n) in the range between 8 and 100, may be utilized in the process. Another compound which can supply paraformaldehyde in-situ is 1,3,5-trioxane. A slight molar excess of formaldehyde in the reaction is usually beneficial, i.e., up to 1.2:1 relative to the pyrazole starting material.

An alkaline environment (for example, pH in the range from 9 to 11), even though not mandatory, greatly favors the reaction. Suitable bases for generating the alkaline environment in the reaction mixture include alkali metal hydroxides, alkali metal carbonates, alkali metal hydrogen carbonates, alkali metal alkoxides, alkali metal hydrides, alkali metal phosphates, and where applicable the corresponding alkaline earth bases. The alkaline agents can be added to the reaction vessel either in a solid form, or as a concentrated aqueous solution. Organic bases, namely, pyridine derivatives and alkylamines can be used instead of the inorganic bases. The amount of the base is in the range of 5:100-300:100 relative to the pyrazole starting material.

The thiomethylation reaction involving the use of the HCHO/M-S—C(O)—$R_2$ couple takes place in water or in an organic solvent, i.e., protic solvents, polar aprotic solvents including halogenated hydrocarbons and aromatic solvents, and mixtures thereof. Aqueous solvents, i.e., water alone and solvent mixtures consisting of water and water miscible organic solvent, particularly polar aprotic solvent, e.g., acetonitrile, dimethylformamide, were found to be useful. Other classes of organic solvents are also suitable, e.g., aqueous mixtures of lower alkanols or ethers. Such mixtures, e.g. water/acetonitrile, can also be used to supply the pyrazole of Formula II to the reaction vessel in the form of a solution, to facilitate the feeding of the reactants to the reaction vessel. Thus, a suitably proportioned reaction medium consists of water/organic solvent at 9:1-1:9 weight ratio. Roughly equally proportioned solvent mixtures, or perhaps with slight water predominance, are usually preferred.

The reactants and reagents can be added in succession to the reaction vessel; simultaneous feeding of two or more reactants is also workable. No particular requirements are placed on the order of addition, with the exception that the pyrazole starting material is brought into contact with the formaldehyde source in the reaction vessel in an alkaline environment, or in the presence of at least a portion of the compound M-S—C(O)—$R_2$, that was previously charged to the reaction vessel.

To cope with this requirement, a sequential addition in which the pyrazole of Formula II is the last added reactant could be applied. For example, the experimental results reported below indicate that the thiomethylation reaction progresses effectively via the slow addition of the pyrazole of Formula II (preferably solubilized in water, organic solvent or a mixture thereof) to a reaction vessel that was previously charged with a compound of the formula M-S—C(O)—$R_2$, formaldehyde source and the base. For example, on a laboratory scale, addition rate whereby the pyrazole is added over a period of 30 minutes to 10 hours is amenable to the process.

One specific aspect of the invention is therefore a process comprising charging a reaction vessel with water, an organic solvent or a mixture thereof, dissolving the compound M-S—C(O)—$R_2$ and the paraformaldehyde in an alkaline environment (generated by the addition of a base), gradually feeding the pyrazole of Formula II, i.e., as a liquid stream consisting of the pyrazole solubilized in water, in said organic solvent or in a mixture thereof, allowing the reaction to reach completion and recovering the reaction product of Formula III (e.g., compound 3).

The reaction advances under stirring at temperature in the range from −20 to 80° C., most conveniently between 0 and 25° C., e.g., around 15° C., with progressive addition of pyrazole, and reaches completion essentially at the end of addition period. The reaction mixture may be kept under stirring for an additional time. The reaction mixture is then worked-up to recover the product of Formula III, e.g., by removal of the organic solvent, if present, and acidification of the aqueous medium, with the aid of a mineral or organic acid (e.g., acetic acid) to precipitate the reaction product of Formula III, which is then separated from the liquid phase (e.g., by filtration), washed with water and dried.

Thiomethylation of the pyrazole of Formula II with the aid of HCHO/M-S—C(O)—$R_2$ couple requires fairly simple workup procedure to collect the reaction product in a solid form, demonstrating high yield. The reaction product, namely, the compound of Formula III, especially thioacetic acid S-(5-hydroxy-1-methyl-3-trifluoromethyl-1H-pyrazol-4-yl-methyl) ester of Formula 3:

3

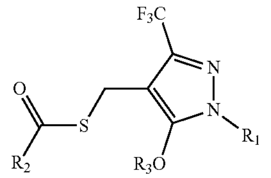

constitutes an additional aspect of the invention. It may be used in the next step of the sequential reaction without further purification, or may be purified, e.g., by crystallization, trituration etc.

It should be noted that for accomplishing the thiomethylation reaction, the invention further contemplates the use of other binary reagent systems:

$H_2C(OR_4)_2$/M-S—C(O)—$R_2$ couple ($R_4$ is alkyl, perfluoroalkyl or aryl);

$H_2C(CO_2R_4)_2$/M-S—C(O)—$R_2$ couple ($R_4$ is alkyl, perfluoroalkyl or aryl); and $CH_2$═$NR_5$/M-S—C(O)—$R_2$ ($R_5$ is alkyl, perfluoroalkyl, aryl, —$SO_2R'$ or —C(O)R' (R' is alkyl, perfluoroalkyl alkyl or aryl).

As an alternative to the thiomethylation reaction based on the use of the HCHO/M-S—C(O)—$R_2$ couple, pyrazole of Formula II can be straightforwardly thiomethylated with the aid of a single reagent of the formula X—$CH_2$—S—C(O)—$R_2$ or a salt thereof, wherein $R_2$ is as defined above (for example, —$CH_3$, —$CH_2C_6H_5$), X is hydroxy or a leaving group, preferably selected from the group consisting of halide (such as chloride or bromide), —O—$SO_2R'$ (R' is alkyl, perfluoroalkyl or aryl), —O—C(O)R' (R' is alkyl, perfluoroalkyl or aryl), —$N^+R'_3$ (R' is hydrogen and alkyl; the quaternary ammonium ion may be part of a ring system). The reagent of the formula X—$CH_2$—S—C(O)—$R_2$ is used in molar excess relative to the pyrazole of Formula II, for example, up to 50%. Illustrative reagents include:

HO—$CH_2$—S—C(O)—$CH_3$ (S-hydroxymethyl ethanethioate; described in *Angew. Chem. Int. Ed.* 2017, 56, 9891);

Br—$CH_2$—S—C(O)—$CH_3$ (S-bromomethyl ethanethioate, described in *Angew. Chem. Int. Ed.* 2017, 56, 9891); and

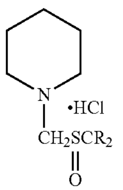

($R_2$ is methyl or benzyl; described in *The Journal of Organic Chemistry* 1965 30 (1), 300-301).

Different types of solvents can be utilized for the reaction, e.g., ethers (including cyclic ethers such as tetrahydrofuran and dioxane), aliphatic alcohols, halogenated hydrocarbons, and polar aprotic solvents such as dimethylformamide, and optionally aqueous mixtures thereof. The reaction is preferably carried out under inert gas atmosphere, optionally with heating.

For example, pyrazole of Formula II is thiomethylated with S-bromomethyl ethanethioate or S-(1-piperidinylmethyl) ethanethioate hydrochloride in dioxane at temperature in the range from 50° C. to reflux. The reaction mixture is then subjected to extractive workup and chromatography to recover the compound of Formula III.

III→IV (e.g., 3→4)

The thioester of Formula III, where $R_3$ is hydrogen, undergoes difluoromethylation of the alcohol functionality at position 5 of the pyrazole ring, creating the corresponding etherified thioester of Formula IV,

IV

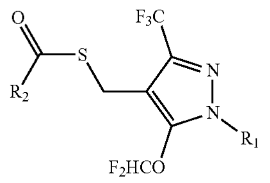

wherein $R_1$ and $R_2$ are as previously defined; specifically difluoromethylation of 3 to give 4:

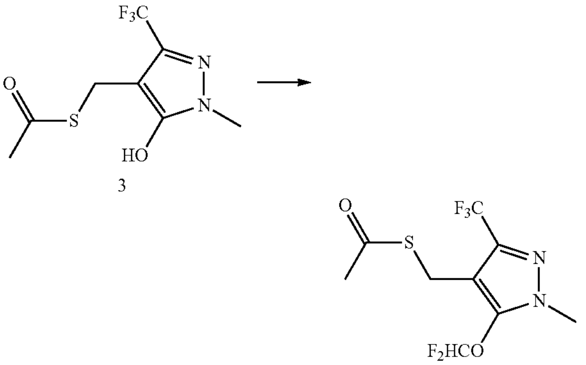

3

4

To this end, the thioester of Formula III where $R_3$ is hydrogen is reacted with a difluoromethylation reagent in an organic solvent, usually in the presence of a base. Operative difluoromethylation reagents are described, for example, by Hu et al. in Chem. Commun. 2009, p. 7465-7478.

Most conveniently, the incorporation of the $F_2HC$— into the alcohol functionality is achieved with the aid of a compound of the formula $F_2X'C-L_1$, wherein X' is hydrogen or halogen (Cl, Br) and $L_1$ is a leaving group. $L_1$ is preferably chlorine, bromine or iodine. $L_1$ can also be:

—COOR", where R" is alkyl group such as methyl or ethyl, or a corresponding alkali metal, e.g., reagents such as $ClCF_2COOMe$, $ClCF_2COONa$ and $BrCF_2COOEt$ can be used;

—C(O)R"', where R"' is alkyl or phenyl; e.g., a reagent such as $ClCF_2C(O)Ph$ can be used;

—P(O) (O-alkyl)$_2$, e.g., reagent such as $BrCF_2PO(OEt)_2$ can be used.

Preferred reagent is $F_2HC-L_1$, especially chlorodifluoromethane. Displacement of $L_1$ in $F_2HC-L_1$ by the action of thioester of Formula III in strongly basic conditions can take place in different solvents [polar aprotic solvents, such as dimethylformamide, dimethylacetamide, acetonitrile and dimethyl sulfoxide, cyclic carbonates (propylene carbonate, ethylene carbonate) and NMP are generally preferred] in the presence of a base (alkali metal hydroxides, alkali metal carbonates, alkali metal hydrogen carbonates, alkali metal alkoxides, alkali metal hydrides, alkali metal phosphates, nitrogen-containing organic bases, namely, trialkylamines and pyridine derivatives) or treatment with sodium metal. The difluoromethylation reagent, e.g., $F_2HC-L_1$ is preferably used in excess. The amount of the base introduced to the reaction vessel is preferably from 1 to 10 equivalents to one equivalent of the thioester of Formula III.

The formation of the etherified thioester of Formula IV is generally conducted under heating, say, from 40 to 100° C. The reaction can be facilitated by addition of a catalyst, e.g., quaternary ammonium salts with halide counter ions, such as tetraalkylammonium bromide or iodide (e.g., tetra-n-butylammonium bromide or iodide) and inorganic iodide salts. Catalytically effective amount, by which such compounds are employed, is from 0.01:1-10:1 relative to thioester of Formula III.

Although formation of the etherified thioester of Formula IV in an open reactor under continuous or intermittent sparging of chlorodifluoromethane through the liquid reaction mixture is quite satisfactory, a more efficient reaction, taking place under pressure in an autoclave is preferable, using $F_2HC-L_1$ as previously defined, e.g., chlorodifluoromethane as the pressuring agent or in addition, using an inert gas to increase the pressure in the reaction vessel. Thus, the difluoromethylation of the alcohol at position 5 of the pyrazole ring may be carried out at atmospheric pressure or above.

The invention specifically provides a process comprising charging a pressure chamber/autoclave with an organic solvent, a thioester of Formula III and a base, pressuring the autoclave with the difluoromethylation reagent (e.g., $F_2HC-L_1$, such that the internal pressure reaches, say, 1.5 to 100 atmospheres), advancing the reaction under heating and optionally stirring and recovering an etherified thioester of Formula IV from the reaction mixture. The process is not limited to any particular order of addition of reactants/reagents. The solvent of choice for this variant of the difluoromethylation reaction of the thioester of Formula III, carried out at high temperature and elevated pressure, is dimethylformamide, which was shown to give good results, especially in conjunction with an alkali metal carbonate (e.g., sodium carbonate) or alkali metal phosphate base (e.g., tripotassium phosphate).

On cooling the reaction vessel and relieving the pressure, etherified thioester of Formula IV, specifically

4

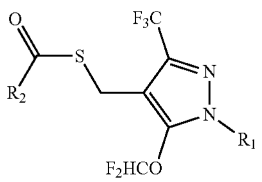

is recovered by conventional techniques, e.g., concentration of the reaction mixture and treatment of the residue with a mixture of water and water-immiscible organic solvent to allow partitioning of the intermediate of Formula IV into the organic solvent, following which the crude product is obtained upon evaporation of the organic layer. The crude ether of Formula IV may proceed to the next step, or can be purified by standard techniques, such as chromatography and/or crystallization, to collect a purified solid intermediate.

The difluoromethylation reaction of a thioester of Formula III using $F_2HC-L_1$ as previously defined, e.g., chlorodifluoromethane, as a pressuring agent in a pressure reactor charged with an organic solvent and a base, proceeds satisfactorily also at ambient/sub-ambient temperature, e.g., below 10° C. Solvents that are suitable for use in this variant of the invention include, in addition to the polar aprotic solvents mentioned above, also aqueous mixtures thereof, and lower alkanols (C1-C3). An especially suitable polar aprotic solvent is a nitrile solvent, e.g., acetonitrile, whereas the preferred base is alkali hydroxide. We have found that such a combination (nitrile solvent and alkali hydroxide) fits well into the ambient/sub-ambient temperature variant of the difluoromethylation reaction.

For example, the thioester of Formula III is added to a pressure reactor that was previously charged with the solvent (e.g., acetonitrile) and alkali hydroxide (e.g., KOH). The reaction mixture is cooled to about −5 to 15° C., e.g., at about 5° C. before the addition of the thioester. The difluoromethylation reagent, e.g., chlorodifluoromethane, is fed gradually to the reactor. On a laboratory scale, the addition rate of chlorodifluoromethane is in the range from 0.1 equivalents per minute to 0.005 equivalents per minute with respect to the thioester of formula III. The reaction mixture is maintained under stirring, e.g., for a few hours, at slightly higher temperature (yet still sub-ambient, e.g., up to 20) and reaches completion. The reaction product is isolated from the reaction mixture using conventional techniques illustrated below.

The thioester of Formula III where $R_3$ is other than hydrogen—namely, $R_3$ is $C_1$ group of the formula $Y_3Y_4HC$— where $Y_3$ and $Y_4$ are both halogen or both alkoxy—can be transformed into a difluoromethyl moiety with a fluorine-containing reagent, i.e., nucleophilic fluoride source such as tetra-n-butylammonium fluoride, pyridine·HF complex or cesium fluoride. In the case where $R_3$ is formyl, it can be transformed into a difluoromethyl moiety via conventional methods of deoxyfluorination, using sulfur tetrafluoride or fluorosulfur complexes.

The ethers of Formula IV, e.g., thioacetic acid S-(5-difluoromethoxy-1-alkyl-3-trifluoromethyl-1H-pyrazol-4-ylmethyl) ester, specifically thioacetic acid S-(5-difluoromethoxy-1-methyl-3-trifluoromethyl-1H-pyrazol-4-ylmethyl) ester (compound 4 depicted above), form additional aspects of the present invention.

It should be noted that the high-temperature conversion of compound 3 to 4 in a pressure reactor (e.g., in DMF as a solvent in the presence of alkali carbonate or phosphate base), and the ambient/low-temperature conversion of compound 3 to 4 (e.g., in acetonitrile as a solvent in the presence of alkali hydroxide base) form additional, standalone aspect of the invention.

IV→I (e.g., 4→1)

Next, the process of the invention comprises a step of reacting the etherified thioester of Formula IV with the 4,5-dihydroisoxazole of Formula V,

V

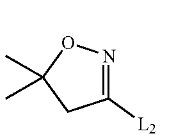

where $L_2$ is a leaving group as previously mentioned above in a different context, specifically halide such as chloride or bromide, to give the sulfide of Formula I, i.e., the preferred reaction is the following:

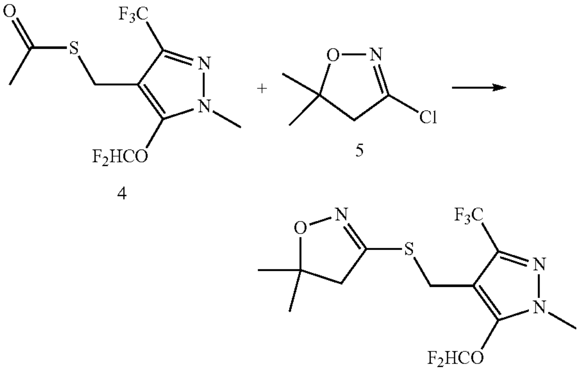

4 5 1

This step of the process comprises charging a reaction vessel with an organic solvent (e.g., lower alkanol, such as MeOH, EtOH and isopropanol, or polar aprotic solvent such as acetonitrile and dimethylformamide or mixtures of these solvents), the reactants of Formula IV (e.g., 4) and V (e.g., 5), a base (alkali metal hydroxides, alkali metal carbonates, alkali metal hydrogen carbonates, alkali metal alkoxides, alkali metals hydrides, alkali metal phosphates, nitrogen-containing organic bases, namely, trialkyl amines and pyridine derivatives), performing the reaction under (optionally) stirring and heating, for example, in refluxing alkanol such as methanol. The progress of the reaction can be tracked by conventional methods of chromatography.

Equimolar amounts of the etherified thioester VI and 4,5-dihydroisoxazole V, or excess of the latter, e.g. up to 50% molar excess are added to the reaction vessel. The amount of the base may vary from 1 to 3 equivalents.

Upon completion of the reaction, the reaction mixture can be worked-up to collect the sulfide of Formula I, e.g., removal of the reaction solvent is followed by repeated extractive procedures using a mixture of water/water immiscible solvent such as ethyl acetate. The organic extracts are combined and washed. Following phase separation and removal of volatile components, the sulfide of Formula I is collected as an oil.

II→III→VI→I (e.g., 2→3→6→1)

As pointed out above, the invention offers an alternative route to the sulfide of Formula I, reversing the order of the difluoromethylation step at position 5 of the pyrazole ring and the step of incorporating the 4,5-dihydroisoxazole into the molecule.

III→VI (e.g., 3→6)

The reaction of thioester of Formula III with 4,5-dihydroisoxazole of Formula V, specifically, the reaction of 3 and 5:

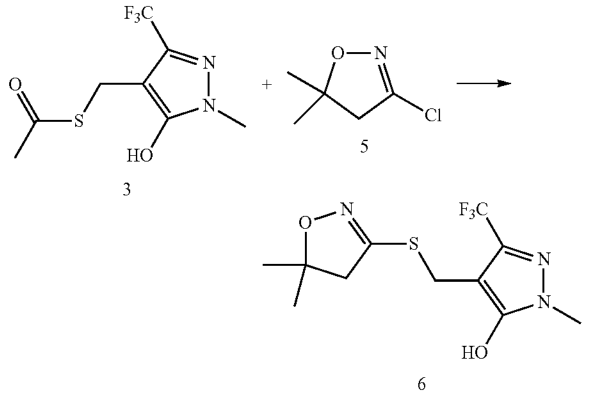

3 5 6 is carried out under conditions akin to those set out above for step IV→I (e.g., 4→1), e.g., in refluxing ethanol, for at least 30 minutes. Workup includes acidification of the reaction mass with aqueous mineral acid followed by extractive procedure as set out above and illustrated in the Working Examples below.

VI→I (e.g., 6→1)

The conditions of the difluoromethylation reaction of VI to give I are as described above for step III→IV (e.g., 3→4).

Lastly, the sulfide of Formula I undergoes oxidation to give the herbicidally active compound, i.e., Pyroxasulfone. The oxidation reaction is accomplished by methods known in the art, using oxidizing agents such as organic and inorganic peroxides; operative oxidizers include hydrogen peroxide, m-chloroperoxybenzoic acid, peroxyacetic acid, peroxybenzoic acid, magnesium monoperoxyphthalate, potassium peroxy monosulfate, potassium permanganate and sodium periodate. As an alternative to direct conversion of the sulfide functionality to sulfone —$SO_2$, one may consider an oxidation reaction passing through the corresponding sulfoxide (—SO), i.e., with isolation of the sulfoxide and subsequent oxidation to the sulfone. The oxidation reaction takes place in organic solvents, or mixtures of organic solvents and water, such as halogenated hydrocarbons (either halogenated aliphatic hydrocarbons such as dichloromethane and chloroform and halogenated aromatic hydrocarbons such as chlorobenzene); ethers such as dioxane, tetrahydrofuran (THF), and diethyl ether; C1-C4 alkanols; ketones; and amides. Illustrative procedures can be found in WO 2004/013106 (≡EP 1541561).

EXAMPLES

Methods

NMR spectrum was recorded with Bruker 400 MHz spectrometer.

Melting point was determined by a Büchi B-545 melting point apparatus.

Example 1

Preparation of thioacetic acid S-(5-hydroxy-1-methyl-3-trifluoromethyl-1H-pyrazol-4-ylmethyl) ester

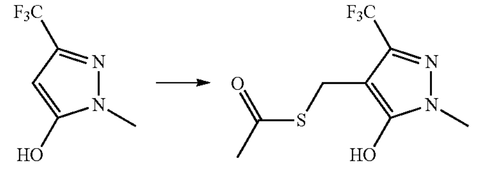

2 3

Potassium thioacetate (31.8 g, 0.278 mol, 1.05 equiv.) was taken up in water (300 g) and acetonitrile (100 g) then paraformaldehyde (10.0 g, 0.333 mol, 1.26 equiv.) and potassium hydroxide (1.56 g, 0.0278 mol, 0.10 equiv.) added. The solution was stirred until dissolution of paraformaldehyde was complete then a solution of 1-methyl-3-(trifluoromethyl)-1H-pyrazol-5-ol (2, 44.0 g, 0.265 mol, 1.0 equiv.) in acetonitrile (200 g) and water (40 g) added over 3 h. Acetonitrile was removed in vacuo at 30° C. and hydrochloric acid (4 M, 130 g) added slowly. The mixture was stirred (15 min) then filtered. The crude product was resuspended in water (200 g) and the mixture stirred (0.5 h) then filtered and dried in vacuo at 25° C. to give the titled compound 3 (64 g, 91%); m.p. 85-87° C.; $^{1}H$ NMR (400 MHz, $CDCl_3$) 9.10 (1H, s), 3.88 (2H, s), 3.68 (3H, s), 2.42 (3H, s); $^{13}C$ NMR (100 MHz, $CDCl_3$) 204.1 (s), 151.0 (s), 137.6 (q, $J_{C-F}$ 37), 121.5 (q, $J_{C-F}$ 270), 96.7 (s), 34.3 (s), 30.5 (s), 22.2 (s); $^{19}F$ NMR (376 MHz, $CDCl_3$)-62.3 (3 F, s).

Example 2

Preparation of thioacetic acid S-(5-hydroxy-1-methyl-3-trifluoromethyl-1H-pyrazol-4-ylmethyl) ester

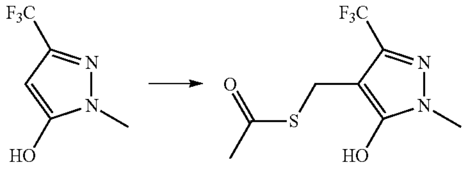

2

3

S-hydroxymethyl ethanethioate (1.92 g, 18.1 mmol, 1.5 equiv.; synthesized according to literature procedures in Z. Sofer, J. Luxa, D. Bouša, D. Sedmidubský, P. Lazar, T. Hartman, H. Hardtdegen, M. Pumera, *Angew. Chem. Int. Ed.* 2017, 56, 9891) was taken up in water (200 g) then a solution of 1-methyl-3-(trifluoromethyl)-1H-pyrazol-5-ol (2, 2.0 g, 12.0 mmol, 1.0 equiv.) in DMF (10 g) added over 3 h. The pH was adjusted to 2 with hydrochloric acid (4 M) then brine (50 mL) added. The product was extracted with (3×50 mL). Volatile components were removed in vacuo to give compound 3 (3.78 g, 82%).

Example 3

Preparation of thioacetic acid S-(5-hydroxy-1-methyl-3-trifluoromethyl-1H-pyrazol-4-ylmethyl) ester

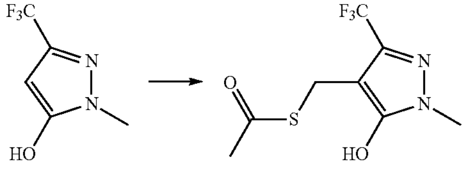

2

3

S-bromomethyl ethanethioate (2.34 g, 13.8 mmol, 1.15 equiv.; synthesized according to literature procedures in Z. Sofer, J. Luxa, D. Bouša, D. Sedmidubský, P. Lazar, T. Hartman, H. Hardtdegen, M. Pumera, *Angew. Chem. Int. Ed.* 2017, 56, 9891) was taken up in alumina-dried dioxane (50 g) then 1-methyl-3-(trifluoromethyl)-1H-pyrazol-5-ol (2, 2.0 g, 12.0 mmol, 1.0 equiv.) added. The solution was stirred under a nitrogen atmosphere at 80° C. (2 h) then concentrated to ca. 10 mL and water (100 g) added. The pH was adjusted to 2 with hydrochloric acid (4 M) then brine (50 mL) added. The product was extracted with $^i$PrOH/$CH_2Cl_2$: ⅕ (3×50 mL). Volatile components were removed in vacuo to give compound 3 (2.26 g, 64%).

Example 4

Preparation of thioacetic acid S-(5-hydroxy-1-methyl-3-trifluoromethyl-1H-pyrazol-4-ylmethyl) ester

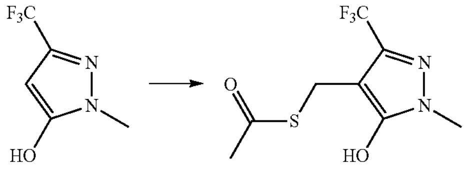

2

3

S-(1-piperidinylmethyl) ethanethioate hydrochloride (2.67 g, 12.7 mmol, 1.06 equiv.; synthesized according to the literature procedure in Edward E. Smissman and John R. J. Sorenson, *The Journal of Organic Chemistry* 1965 30 (1), 300-301) was taken up in alumina-dried dioxane (50 g) then 1-methyl-3-(trifluoromethyl)-1H-pyrazol-5-ol (2, 2.0 g, 12.0 mmol, 1.0 equiv.) added. The solution was stirred under a nitrogen atmosphere at 80° C. (2 h) then concentrated to ca. 10 mL and water (100 g) added. The pH was adjusted to 2 with hydrochloric acid (4 M) then brine (50 mL) added. The product was extracted with $^i$PrOH/$CH_2Cl_2$: ⅕ (3×50 mL). Volatile components were removed in vacuo to give compound 3 (2.14 g, 66%).

Example 5

Preparation of thioacetic acid S-(5-difluoromethoxy-1-methyl-3-trifluoromethyl-1H-pyrazol-4-ylmethyl) ester

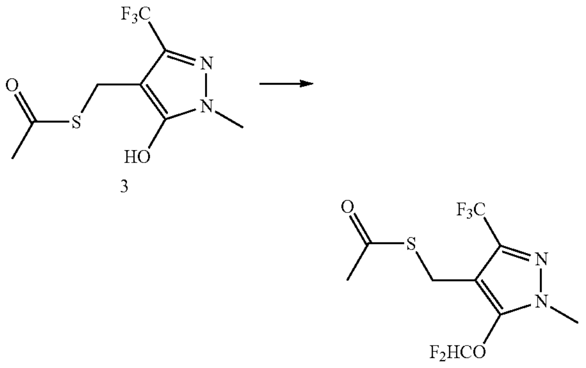

3

4

Compound 3 (4.0 g, 0.016 mol, 1.0 equiv.) was taken up in DMF (80 g) and sodium carbonate (5.0 g, 0.047 mol, 3.0 equiv.) added. The mixture was pressurized with chlorodifluoromethane, in a 400 mL autoclave, with stirring, to a pressure of 2.5 atmospheres. The mixture was heated to 80° C., with stirring (3 h). Heating was stopped and the reaction stirred, allowing to cool to ambient temperature. The autoclave was vented to the atmosphere then the mixture was concentrated in vacuo to an approximate weight of 12 g. Water (50 g) and hexane (50 g) were added and the mixture stirred vigorously (15 min). The mixture was partitioned and the hexane partition concentrated in vacuo to give a crude sample of compound 4 as an orange oil (3.63 g, 76%), which was used without further purification. An analytical sample of 4 was obtained by flash column chromatography on silica, eluting with EtOAc/hexanes: ¼; m.p. 33-35° C.; $^{1}H$ NMR (400 MHz, $CDCl_3$) 6.68 (1H, t, $J_{H-F}$ 72), 4.04 (2H, s, $CH_2$), 3.81 (3H, s, $CH_3$), 2.35 (3H, s, $CH_3$); $^{13}C$ NMR (100 MHz, $CDCl_3$) 194.7 (s), 142.8 (s), 139.0 (q, $J_{C-F}$ 37), 120.9 (q, $J_{C-F}$ 270), 115.6 (t, $J_{C-F}$ 270), 104.9 (s), 35.8 (s), 30.1 (s), 20.1 (s); $^{19}F$ NMR (376 MHz, $CDCl_3$)-62.3 (3 F, s), −81.6 (2 F, d, $J_{H-F}$ 72).

Example 6

Preparation of thioacetic acid S-(5-difluoromethoxy-1-methyl-3-trifluoromethyl-1H-pyrazol-4-ylmethyl) ester

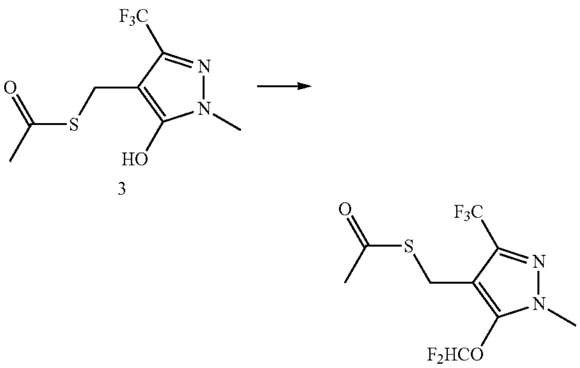

3

4

Compound 3 (7.30 g, 28.7 mmol, 1.0 equiv.) was added to DMF (70 g) and tripotassium phosphate (11.9 g, 86.1 mmol, 3.0 equiv.). The mixture was pressurized with chlorodifluoromethane, in a 400 mL autoclave, with stirring, to a pressure of 5 atmospheres. The mixture was heated to 80° C., with stirring (3 h). Heating was stopped and the reaction stirred, allowing to cool to ambient temperature. The autoclave was vented to the atmosphere then the mixture was drained into a mixture of water (300 g) and hexane (100 g). The mixture was stirred vigorously (15 min). The mixture was allowed to separate. The organic (upper) partition was collected and the lower (aqueous) partition was washed with hexane (50 g). This hexane wash was combined with the previously collected organic (upper) partition and this combined hexane fraction washed with water (100 mL) then concentrated in vacuo to give compound 4 as an orange oil (8.71 g, 80 purity, 79% yield), which was used without further purification.

Example 7

Preparation of thioacetic acid S-(5-difluoromethoxy-1-methyl-3-trifluoromethyl-1H-pyrazol-4-ylmethyl) ester

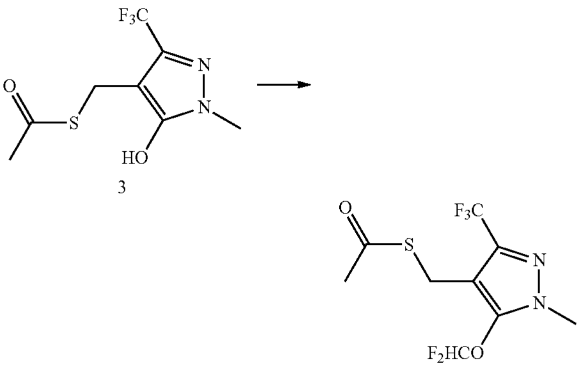

3

4

A pressure vessel was charged with potassium hydroxide (13.3 g, 0.24 mol, 2.0 equiv.) and acetonitrile (100 mL) and cooled to 5° C. Compound 3 (30 g, 0.12 mol, 1.0 equiv.) was added at 5° C. and the slurry stirred for 15 minutes. The reaction mixture was charged continuously with chlorodifluoromethane (30.6 g, 0.35 mol, 3.0 equiv.), over 3 hours, at 5° C. The reaction mixture was allowed to warm to 10° C. and stirred for 5 hours at this temperature. Ethyl acetate (100 mL) and water (200 mL) were added and stirring continued for 20 minutes at 10° C. Stirring was stopped and the mixture allowed to separate into an organic and aqueous partition. The aqueous partition was extracted with ethyl acetate (100 mL) and the ethyl acetate extract combined with the organic partition of the reaction mixture and washed with water (2×100 mL). The volatile components of the mixture were removed in vacuo to give Compound 4 (32.3 g, 90% purity, 81%).

Example 8

Preparation of 3-[[[5-(Difluoromethoxy)-1-methyl-3-(trifluoromethyl)-1H-pyrazol-4-yl]methyl]thio]-4,5-dihydro-5,5-dimethylisoxazole

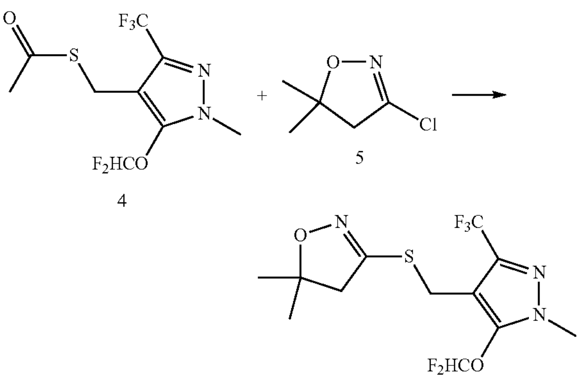

4

5

1

Compound 4 (1.31 g, 80% purity, 3.4 mmol, 1.0 equiv.) was taken up in methanol (20 g) and 3-chloro-5,5-dimethyl-4,5-dihydroisoxazole (5, 0.63 g, 4.7 mmol, 1.4 equiv.) then sodium carbonate (1.37 g, 13 mmol, 3.8 equiv.) added. The mixture was heated to 50° C., with stirring (6 h). Methanol (10 mL) was removed in vacuo and water (100 g) added. The mixture was extracted with ethyl acetate (2×30 g). The combined ethyl acetate extracts were washed with water (100 mL), brine (50 mL) and volatile components removed in vacuo to give 1 as a yellow oil (1.62 g, 59% purity, 78% yield).

Example 9

Preparation of 3-[[[5-(hydroxy)-1-methyl-3-(trifluoromethyl)-1H-pyrazol-4-yl]methyl]thio]-4,5-dihydro-5,5-dimethylisoxazole

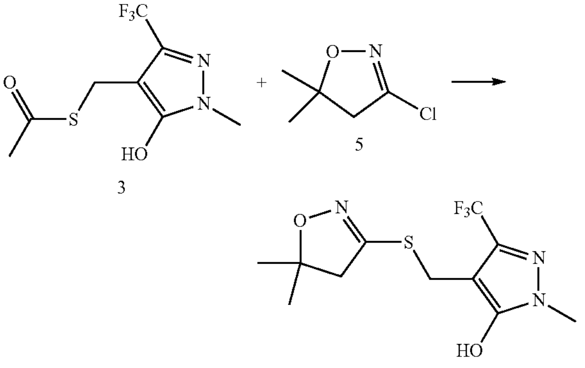

3 5 6

Compound 3 (0.50 g, 2.0 mmol, 1.0 equiv.) was taken up in ethanol (10 g) and 3-chloro-5,5-dimethyl-4,5-dihydroisoxazole (5, 0.30 g, 2.2 mmol, 1.1 equiv.) then potassium carbonate (0.54 g, 3.9 mmol, 2.0 equiv.) added. The mixture was heated to reflux, with stirring (16 h). The mixture was acidified to pH 3 with 1 M HCl. The resulting mixture was then extracted with ethyl acetate (2×50 g). The combined ethyl acetate extracts were washed with hydrochloric acid (1 M, 100 mL), brine (50 mL) and volatile components removed in vacuo to give 6 as a yellow oil (385 mg, 79% purity, 50% yield).

The invention claimed is:

1. A process which comprises the step of reacting a pyrazole of Formula II:

II

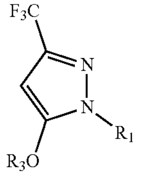

to create an $R_2$—C(O)—S—$CH_2$— functionality at position 4 of the pyrazole ring, thereby obtaining, and optionally isolating, a thioester of Formula III

III

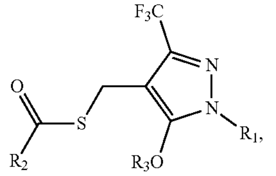

where:

$R_1$ is $C_1$-$C_3$ alkyl;

$R_2$ is a hydrogen-bearing group $Y_2Y_1H^*C^*$—, where the α carbon and α hydrogen are denoted by asterisks, in which $Y_1$ and $Y_2$ are independently selected from hydrogen, $C_1$-$C_2$ alkyl and —$C_6H_5$; and $R_3$ is hydrogen or $C_1$ group, said $C_1$ group being $Y_3Y_4HC$— where $Y_3$ and $Y_4$ are halogen or alkoxy, or said $Y_3$ and $Y_4$ are taken together to be ═O.

2. A process according to claim 1, wherein $R_2$ is —$CH_3$ and $R_3$ is hydrogen.

3. A process according to claim 1, comprising reacting pyrazole of Formula II with a compound of the formula M-S—C(O)—$R_2$, wherein M is hydrogen or a metal cation and $R_2$ is as defined, in the presence of formaldehyde source in an alkaline environment.

4. A process according to claim 3, wherein the pyrazole of Formula II is brought into contact with the formaldehyde source in a reaction vessel following the creation of an alkaline environment, or in the presence of at least a portion of the compound M-S—C(O)—$R_2$ which was previously charged to the reaction vessel.

5. A process according to claim 4, comprising charging a reaction vessel with water or an organic solvent or a mixture thereof, adding the compound M-S—C(O)—$R_2$ and dissolving paraformaldehyde in an alkaline environment generated by addition of a base, gradually feeding the pyrazole of Formula II, allowing the reaction to reach completion and recovering the reaction product of Formula III.

6. A process according to claim 1, wherein the pyrazole of Formula II is thiomethylated with the aid of a reagent of the formula X—$CH_2$—S—C(O)—$R_2$ or a salt thereof, wherein $R_2$ is as defined above, and X is a leaving group or hydroxy.

7. A process according to claim 6, wherein the reagent of the formula X—$CH_2$—S—C(O)—$R_2$ is selected from the group consisting of:

HO—$CH_2$—S—C(O)—$CH_3$;

Br—$CH_2$—S—C(O)—$CH_3$; and

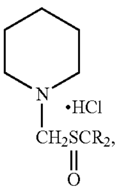

wherein $R_2$ is methyl or benzyl.

8. A process according to claim 1, wherein the pyrazole of Formula II is:

2

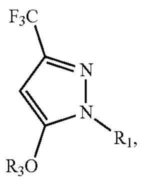

and the thioester of Formula III is:

3

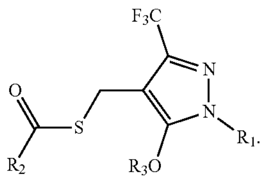

9. A process according to claim 1, further comprising the step of reacting thioester of Formula III where $R_3$ is hydrogen with a difluoromethylation reagent, thereby forming, and optionally isolating, the corresponding etherified thioester of Formula IV

IV

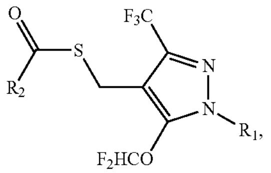

wherein $R_1$ and $R_2$ are as previously defined.

10. A process according to claim 9, wherein the difluoromethylation reagent is $F_2X'C-L_1$, wherein X' is hydrogen or halogen and $L_1$ is a leaving group.

11. A process according to claim 10, wherein the difluoromethylation reagent is a compound of formula $F_2HC-L_1$.

12. A process according to claim 11, comprising charging an autoclave with an organic solvent, a thioester of Formula III and a base, pressuring the autoclave with $F_2HC-L_1$, advancing the reaction under heating and optionally stirring and recovering the etherified thioester of Formula IV from the reaction mixture.

13. A process according to claim 12, wherein the organic solvent is dimethylformamide and the base is an alkali metal carbonate or an alkali metal phosphate.

14. A process according to claim 11, comprising charging an autoclave with an organic solvent, a thioester of Formula III and a base, pressuring the autoclave with $F_2HC-L_1$, wherein the reaction temperature is below 10° C., and recovering the etherified thioester of Formula IV from the reaction mixture.

15. A process according to claim 14, wherein the organic solvent is acetonitrile and the base is an alkali metal hydroxide, and the reaction mixture is cooled to less than 10° C.

16. A process according to claim 9, wherein the thioester of Formula III is:

3

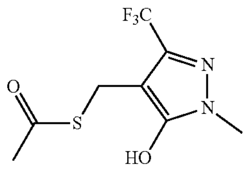

and the etherified thioester of Formula IV is:

4

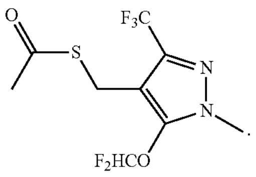

17. A process according to claim 1, further comprising the step of reacting the thioester of Formula III where $R_3$ is a $C_1$ group with a fluorine-containing reagent, thereby forming, and optionally isolating, the corresponding etherified thioester of Formula IV

IV

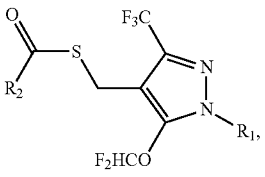

wherein $R_1$ and $R_2$ are as previously defined.

18. A process according to claim 9, further comprising the step of reacting the etherified thioester of Formula IV with the 4,5-dihydroisoxazole of Formula V:

V

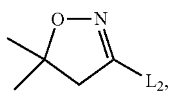

where $L_2$ is a leaving group, to give the sulfide of Formula I:

I

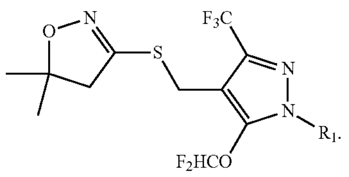

19. A process according to claim 18, wherein the reaction is

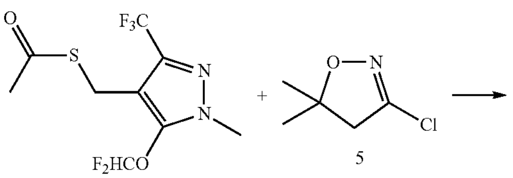

4

5

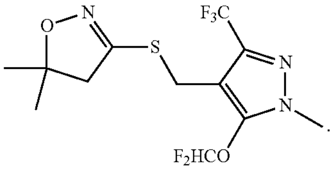

1

20. A process according to claim 1, further comprising the steps of:

reacting the thioester of Formula III:

III

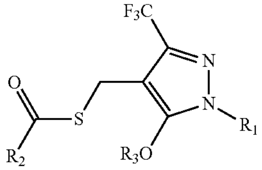

with the 4,5-dihydroisoxazole of Formula V:

V

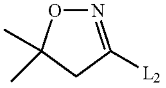

where $L_2$ is a leaving group, to give a compound of Formula VI:

VI

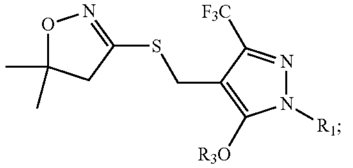

and reacting the compound of Formula VI with a difluoromethylation reagent and recovering a compound of Formula I:

I

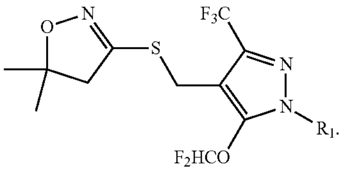

21. A process according to claim 18, further comprising oxidizing the compound of Formula I to the corresponding sulfoxide or sulfone.

22. A process according to claim 21, wherein the oxidation affords pyroxasulfone:

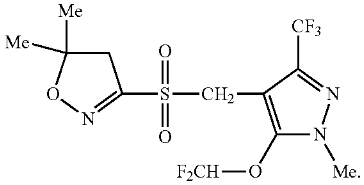

23. A compound of Formula III:

III

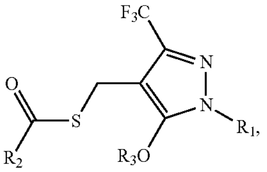

where:

$R_1$ is $C_1$-$C_3$ alkyl;

$R_2$ is α hydrogen-bearing group $Y_2Y_1H^*C^*$—, where the α carbon and a hydrogen are denoted by asterisks, in which $Y_1$ and $Y_2$ are independently selected from hydrogen, $C_1$-$C_2$ alkyl and —$C_6H_5$; and $R_3$ is hydrogen or $C_1$ group, said $C_1$ group being $Y_3Y_4HC$—, where $Y_3$ and $Y_4$ are halogen or alkoxy, or said $Y_3$ and $Y_4$ are taken together to be =O.

24. A compound according to claim 23, which is:

3

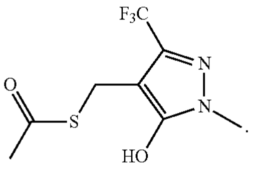

25. A compound of Formula IV:
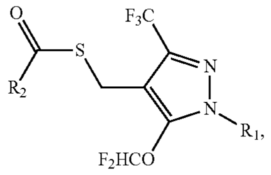
IV
where:
$R_1$ is $C_1$-$C_3$ alkyl; and
$R_2$ is α hydrogen-bearing group $Y_2Y_1H^*C^*$—, where the α carbon and a hydrogen are denoted by asterisks, in which $Y_1$ and $Y_2$ are independently selected from hydrogen, $C_1$-$C_2$ alkyl and —$C_6H_5$.
26. A compound according to claim 25, which is:
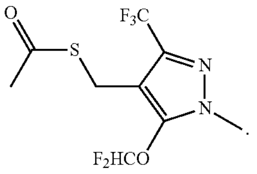
4
* * * * *